(12) United States Patent
Kabeer (10) Patent No.: US 9,452,206 B2
(45) Date of Patent: Sep. 27, 2016

(54) ISOLATION OF LYMPHOCYTES AND DELIVERY TO SPLENECTOMY PATIENTS

(71) Applicant: Children's Hospital of Orange County, Orange, CA (US)

(72) Inventor: Mustafa Kabeer, Irvine, CA (US)

(73) Assignee: CHILDREN'S HOSPITAL OF ORANGE COUNTY, Orange, CA (US)

( * ) Notice: Subject to any disclaimer, the term of this patent is extended or adjusted under 35 U.S.C. 154(b) by 0 days.

(21) Appl. No.: 13/973,896

(22) Filed: Aug. 22, 2013

(65) Prior Publication Data

US 2014/0056944 A1 Feb. 27, 2014

Related U.S. Application Data

(60) Provisional application No. 61/693,180, filed on Aug. 24, 2012.

(51) Int. Cl.
| | | |
|---|---|---|
| A61K 39/09 | (2006.01) | |
| A61K 39/00 | (2006.01) | |
| A61K 35/26 | (2015.01) | |

(52) U.S. Cl.
CPC ............ *A61K 39/092* (2013.01); *A61K 35/26* (2013.01); *A61K 39/00* (2013.01)

(58) Field of Classification Search
None
See application file for complete search history.

(56) References Cited

U.S. PATENT DOCUMENTS

| 4,529,694 A | * | 7/1985 | Lazarus et al. ............ 435/70.21 |
|---|---|---|---|
| 4,828,395 A | | 5/1989 | Saito et al. |
| 2004/0252582 A1 | | 12/2004 | Bucher |
| 2005/0058019 A1 | | 3/2005 | Jahn et al. |
| 2005/0139704 A1 | | 6/2005 | Liao et al. |
| 2010/0116744 A1 | | 5/2010 | Vitzthum |

FOREIGN PATENT DOCUMENTS

| CA | 21668263 | * | 2/1995 | ............ A61K 35/14 |
|---|---|---|---|---|
| WO | WO 94/20124 A1 | | 9/1994 | |

OTHER PUBLICATIONS

Tassone et al. (Chapter 20, pp. 351-357, Christiansen et al. Immunogenetics Apr. 2012).*
Breukels et al. (Infection of Immunity vol. 69, No. 12, 2001).*
International Search Report and Written Opinion re International Application No. PCT/US2013/056517, mailed Nov. 20, 2013, in 15 pages.
Oakes D. D. et al: "Intraportal splenic autotransplantation in rats: Feasibility and effectiveness", Journal of Surgical Research, Academic Press Inc., San Diego. CA. US, vol. 32, No. 1, Jan. 1, 1982, pp. 7-14, XP026299981, ISSN: 0022-4804, DOI: 10.1016/0022-4804(82)90178-0.
Pisters P. W. T. et al: "Autologous 5-11 Splenic Transplantation for Splenic Trauma ", Annals of Surgery, vol. 219, No. 3, Mar. 1, 1994, pp. 225-235, XP055203332, ISSN: 0003-4932, DOI: 10.1097/00000658-199403000-00002.
Leemans R. et al: "Spleen autotransplantation provides restoration of functional splenic lymphoid compartments and improves the humoral immune response to pneumococcal polysaccharide vaccine", Clinical & Experimental Immunology, vol. 117, No. 3, Sep. 1, 1999, pp. 596-604, XP055203557, ISSN: 0009-9104, DOI: 10.1046/j.1365-2249.1999.00943.x.
Zandvoort A. et al: "The dual function of the splenic marginal zone: essential for initiation of anti-TI-2 responses but also vital in the general first-line defense against blood-borne antigens", Clin Exp Immunol, vol. 130, Jan. 1, 2002, pp. 4-11, XP055203562.
"Post-Splenectomy Vaccine Prophylaxis", 5-11, Jul. 1, 2003, XP055203950.
Communication pursuant to Rule 164(1) EPC dated Jul. 30, 2015 in Application No. EP13830984.
Supplementary Partial European Search Report dated Jul. 30, 2015 in Application No. EP13830984.

* cited by examiner

*Primary Examiner* — J. Hines
*Assistant Examiner* — Khatol Shahnan Shah
(74) *Attorney, Agent, or Firm* — Knobbe, Martens, Olson & Bear, LLP (57) ABSTRACT

The present invention includes a method and device for the isolation of lymphocytes, particularly splenic lymphocytes, for administration to patients. In particular for patients undergoing a splenectomy, administration of splenic lymphocytes may increase a patient's immunity and reduce the likelihood of post-splenectomy infections and other complications.

12 Claims, 11 Drawing Sheets

ISOLATION OF LYMPHOCYTES AND DELIVERY TO SPLENECTOMY PATIENTS

BACKGROUND OF THE INVENTION

1. Field of the Invention

The embodiments described herein are directed to methods and devices for the isolation and delivery of cells, such as lymphocytes, to patients, in particular patients undergoing a splenectomy. When administered to a patient, embodiments described herein may increase the patient's immunity and reduce the likelihood of a post-splenectomy infection.

2. Description of the Related Art

There are several medical conditions that often necessitate the removal of all or part of a patient's spleen, for example as a result of physical trauma, spontaneous rupture, malignancy, or enlargement secondary to conditions such as malaria, mononucleosis, or lymphoma. However, patients having undergone splenectomy procedures typically suffer from side effects including reduced immune function and a greater risk of overwhelming post-splenectomy infection ("OPSI") due to sepsis from encapsulated microorganisms. This is a particular risk for patients whose spleens were removed during childhood.

As such, surgical treatment focuses on conserving the spleen if possible, especially when treating pediatric patients. If a splenectomy is required, an attempt may be made to preserve at least a portion of the spleen via a partial splenectomy. However, some cases still necessitate a complete splenectomy.

It can be rationalized that if the spleen serves as a filter to intravascular bacterial contaminants, a possible way of decreasing the risk of OPSI and other post-splenectomy complications would be to save the spleen or to autotransplant sections that can be salvaged. The structure of the spleen is thought to be an integral part involved in immune functionality. The vascular flow through the sinusoids allows antigenic debris to be presented to the resident reticuloendothelial cells lining the sinuses. These cells in turn can present processed antigen to activate other cells within the immune system. It has therefore long been felt that this ambiance of the spleen must be preserved in order to maintain function.

Accordingly, numerous studies have examined the feasibility of autologous splenic transplantation as a possible alternative in unsalvageable cases requiring splenectomy. Improved antibody responses along with increased levels of opsonins and tuftsin have been observed in some experimental models. Certain studies have shown that in order to achieve any benefit in humoral immunity, at least approximately half of the spleen should be retained. Some studies reported that good outcomes resulted from autotransplants within the mesentery in comparison to intramuscular transplants. Additionally, some studies have shown that improved antibody titers were obtained with intraperitoneal autotransplantation of splenic tissue. Further studies have shown an increased survival rate with a 50% splenectomy compared to a total splenectomy, in a mouse model, when exposed to a Streptococcal challenge.

However, splenic autotransplantation is not frequently practiced because of complications such as autotransplant fibrosis, aseptic necrosis, or bowel adhesion and/or obstruction. Such complications may necessitate further surgery. Additionally, there is some experimental evidence of a lack of efficacy of such autotransplants, as certain studies have shown that autotransplanted spleens have been found to undergo approximately 8% necrosis each year, and are therefore soon below optimal efficacy. Aside from function, it has also been noted that transplanted spleen sections have been found to have decreased size of peri-arteriolar lymphatic sheath ("PALS") along with changes in density of B cell, macrophages and T-cell ratios. Not only have changes in parenchymal architecture been observed, but vasculature may also be altered by dilation of vessels in the marginal zone, pulp cords and red pulp where antigen presentation occurs in the spleen.

As stated above, the risks of OPSI are elevated in all splenectomized patients, and the most frequent causes of OPSI include encapsulated organisms, specifically *Streptococcus pneumoniae*. Currently, vaccine and antibiotic prophylaxis are used to help prevent OPSI in splenectomized patients. Although polyvalent pneumococcal vaccines are available and used for prophylaxis in cases of necessary splenectomy, there are cases where patients have still succumbed to fatal sepsis due to OPSI. Additionally, some studies have shown that serum titers against certain pneumococcal subtypes decline over time to nonprotective levels. Rather, although vaccination is most effective if given prior to splenectomy, this is not always possible.

SUMMARY OF THE INVENTION

Accordingly, due to the inability to pre-vaccinate for certain splenectomies, for example those secondary to trauma, and the inefficacy of splenic transplant, embodiments disclosed herein disclose a novel alternative that involves using delivery of lymphocytes, in particular autologous splenic lymphocytes, for cases necessitating splenectomy A first embodiment discloses a method of reducing the likelihood of post-splenectomy infection in a patient, wherein the method comprises:
removing all or part of the patient's spleen;
harvesting lymphocytes from at least a portion of the removed spleen;
administering the harvested lymphocytes to the patient, thereby increasing the patient's immunity and reducing the likelihood of post-splenectomy infection.

In further embodiments, the lymphocytes may be administered intravenously. In some embodiments, the step of harvesting comprises homogenizing at least a portion of the removed spleen and isolating a cellular fraction containing lymphocytes from the homogenized splenic tissue. Some embodiments may further comprise testing at least a sample of the harvested splenic lymphocytes after harvesting for one or more of purity, cellular viability, and cellular counts. In some embodiments, the method further comprises administering an antigen associated with a pathogen subsequent to removal of the spleen from the patient. The antigen may be a vaccine. The method may also improve the vaccine response of the patient. In some embodiments, the improved vaccine response comprises improving the humoral immunity of the patient. In some embodiments, the antigen is administered subcutaneously. In some embodiments, the antigen may be administered intramuscularly, intravenously, or orally. The antigen may comprise a polysaccharide antigen, and may comprise a *Streptococcus pneumoniae* vaccine. In some embodiments, the antibody titer of the patient to the antigen one week after administration of the antigen is elevated.

In another embodiment, a device for the isolation of lymphocytes from tissues comprises:
a top portion comprising a lid and a crank comprising a crankshaft rotatably attached to the lid and extending therethrough in a longitudinal direction, wherein the crank shaft further comprises a grinder implement attached at a distal end of the crankshaft;

a bottom portion comprising a filtering component at the proximal end of the bottom portion; and a middle portion defining a cylindrical body, the middle portion configured to be placed between the top portion and the bottom portion, wherein the top, middle, and bottom portions are joined together to define a cavity therein, and wherein the grinder implement is configured to grind tissue placed within the cavity.

In further embodiments, the device further comprises a handle attached to the crank. In some embodiments, the crank is attached to a motor. In some embodiments, the device comprises a port configured to be connected to a fluid source. In further embodiments, the lid comprises one or more channels in fluidic communication with the port and the cavity to permit the fluid from the port to enter the cavity. In further embodiments, wherein the grinder implement comprises a grinding surface provided with one or more cutting channels. In some embodiments, at least one of the top portion and middle portion, or the middle portion and bottom portion, may be secured together by threads. In some embodiments, the filtering component comprises a sieve. The filtering component may also comprise a membrane filter. In further embodiments, a distal end of the bottom portion is configured to attach to a collection device.

In yet another embodiment, a method of obtaining a population of splenic lymphocytes comprises:

inserting all or part of a spleen tissue into a device for the isolation of lymphocytes, the device comprising a cavity configured to receive the tissue therein, the cavity comprising a grinder implement at a proximal end of the cavity and a filtering component at a distal end of the cavity;

grinding the tissue by pressing and rotating the grinder implement against the tissue;

supplying fluid into the cavity;

filtering the ground tissue and fluid through the filtering component; and collecting the ground tissue and fluid in a receptacle.

In further embodiments, the method further comprises assaying the collected tissue and fluid using flow cytometry. In another embodiment, the method further comprises purifying the population of lymphocytes from the collected tissue and fluid.

DETAILED DESCRIPTION OF THE PREFERRED EMBODIMENT

Embodiments disclosed herein relate to the isolating and delivering lymphocytes, in particular splenic lymphocytes, to patients requiring or desiring to strengthen their immune system. In particular for patients undergoing a splenectomy, such embodiments may serve to reduce the likelihood of a post-splenectomy infection and other such complications. It will be noted that although certain portions of the description herein may refer to animals such as mice, the embodiments described herein may be used in a non-limiting sense in humans and other animals as well. The terminology used in the description presented herein is not intended to be interpreted in any limited or restrictive manner. Rather, the terminology is simply being utilized in conjunction with a detailed description of embodiments of the systems, methods and related components. Furthermore, embodiments may comprise several novel features, no single one of which is solely responsible for its desirable attributes or is believed to be essential to practicing the inventions herein described.

After splenectomy, a patient typically suffers a reduced immunity resulting from a loss of the immune functionality provided by the spleen. Spleen loss may lead not only to a reduced cell-mediated immune response (through T-lymphocytes and other macrophages), but will also a reduced humoral immune response due to a loss of B-lymphocytes, antibodies produced by these B-lymphocytes, and the loss of spleen structure functioning in antigen presentation and removal. Thus, splenectomy may lead to reduced immune response not only because of the loss of splenic structure in mediating the immune response, but also due to the loss of the significant population of cells and other constituents, including lymphocytes, that are present therein. These lymphocytes may include, but are not limited to, B cells (including plasma B cells, memory B cells, and follicular B cells), T cells (including cytotoxic T cells, memory T cells, helper T cells, natural killer T cells, suppressor T cells, and gamma delta T cells), natural killer cells, and progenitor lymphopoietic stem cells.

Accordingly, lymphocytes and other immune-boosting constituents may be isolated from a patient and reintroduced to the patient to boost his or her immune response. Preferably, lymphocytes from the spleen are reintroduced to the patient. While non-autologous or xenotranfused lymphocytes may be used (while accounting for immunologic rejection mechanisms), preferably the source of lymphocytes is from the patient's own spleen.

Device for the Isolation of Lymphocytes

Lymphocytes may be extracted from any tissue containing lymphocytes, and in particular from the spleen or portions thereof, by using embodiments of the devices and methods discussed below. Of course, it will be understood that the device illustrated below can be used for tissue homogenization and/or extraction of cells other than lymphocytes or from sources other than splenic tissue.

Figure 1A:
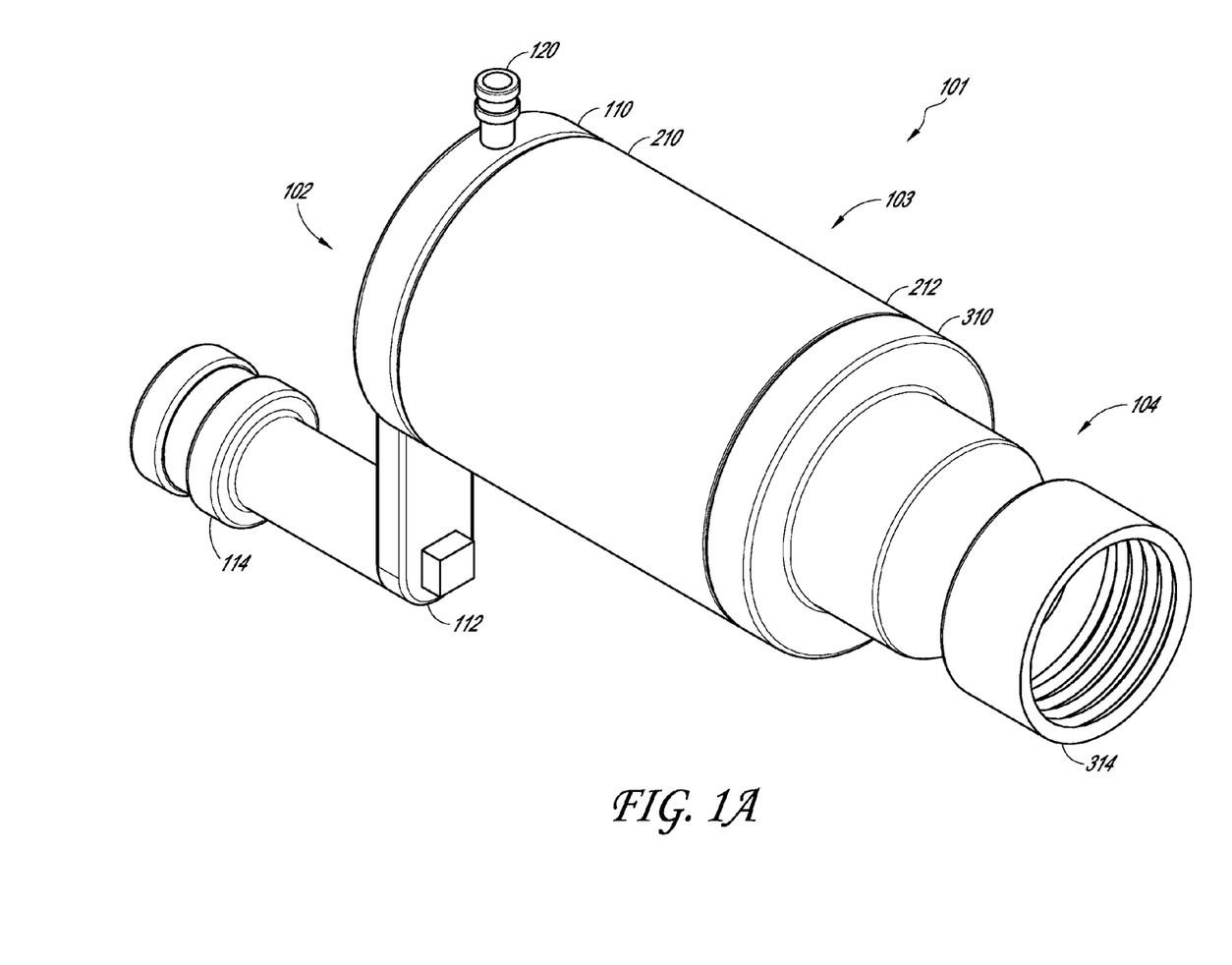
FIGS. 1A-B illustrate perspective views of an embodiment of a tissue grinding device.
Figure 1B:
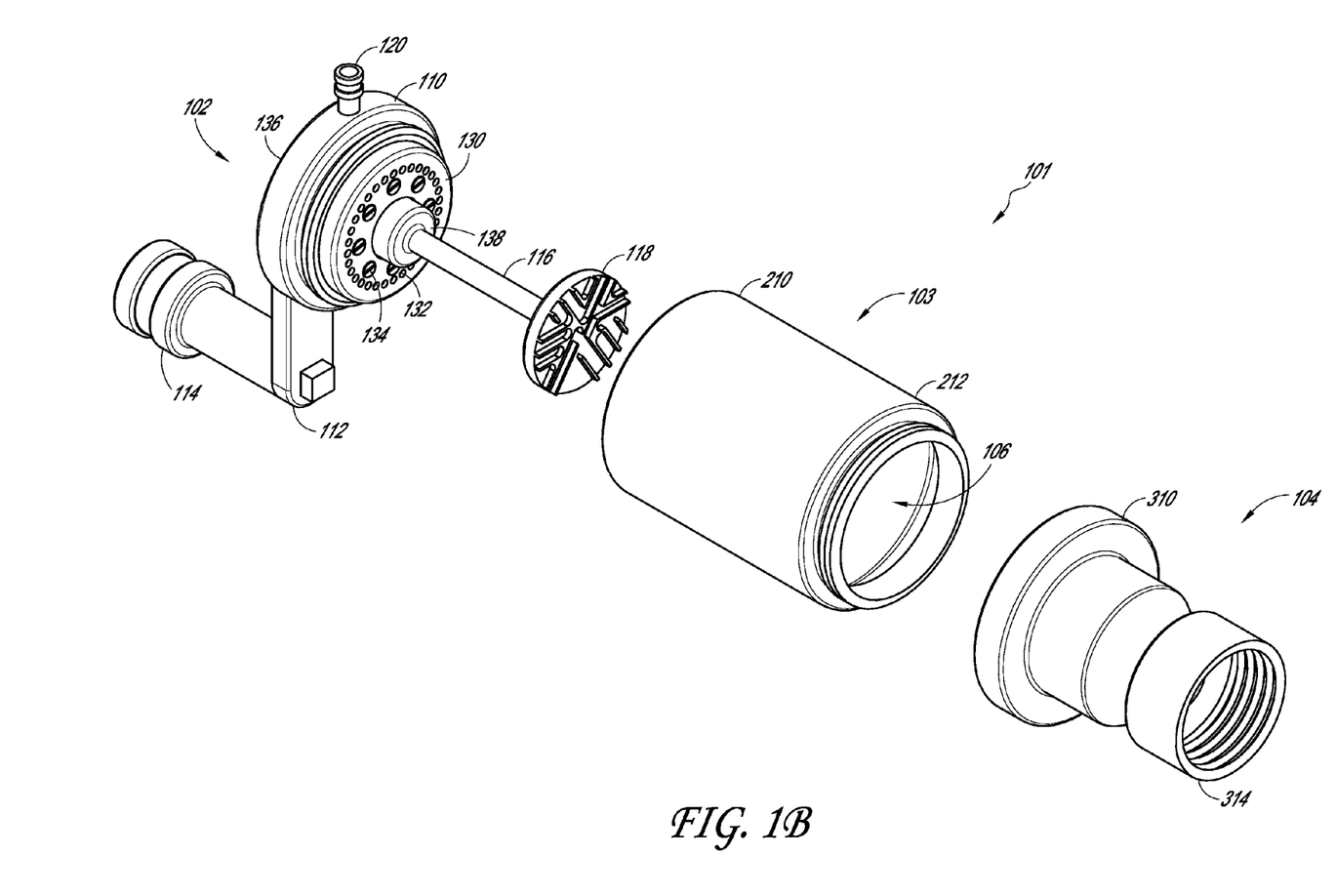
Figure 2A:
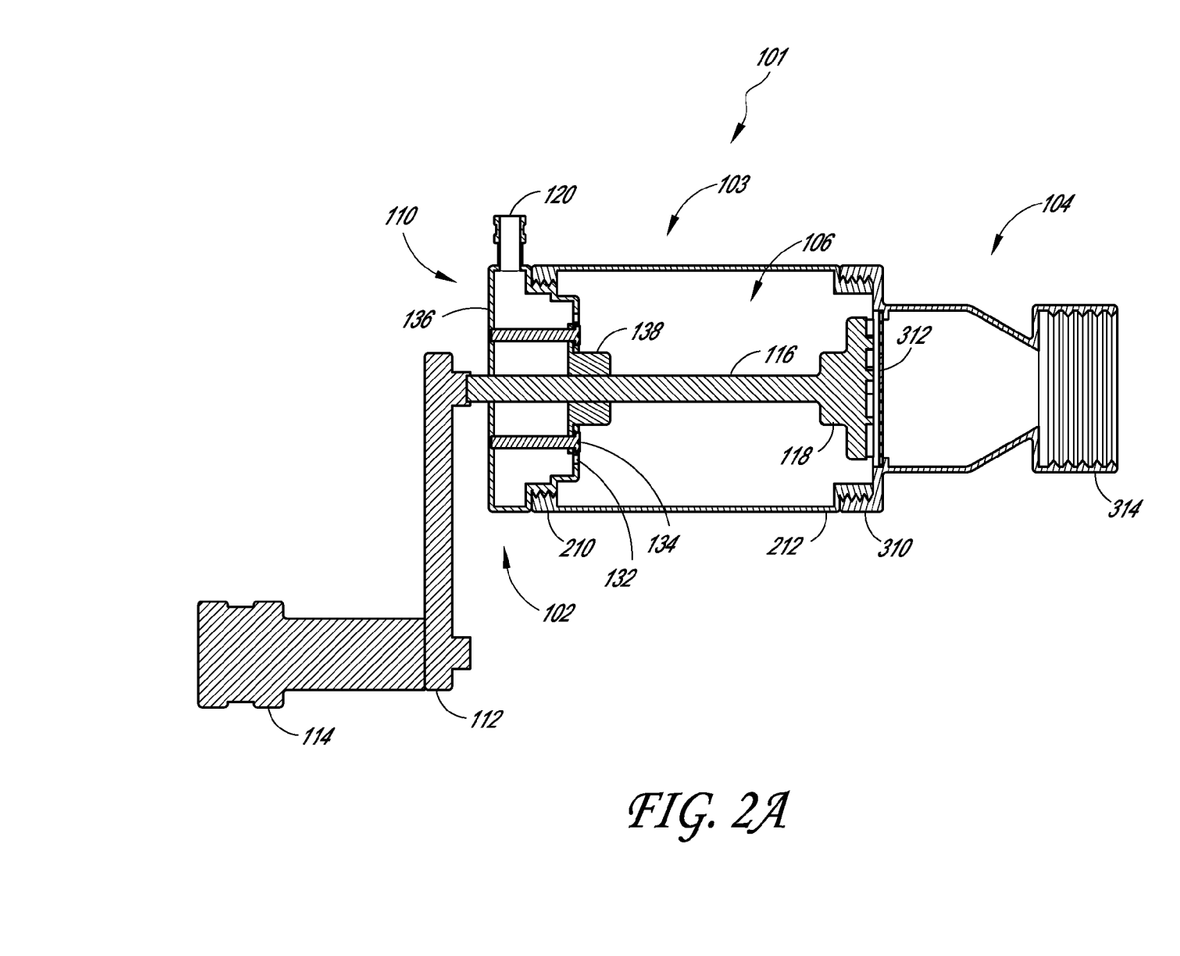
FIGS. 2A-B illustrate cross-sectional views of an embodiment of a tissue grinding device.
Figure 2B:
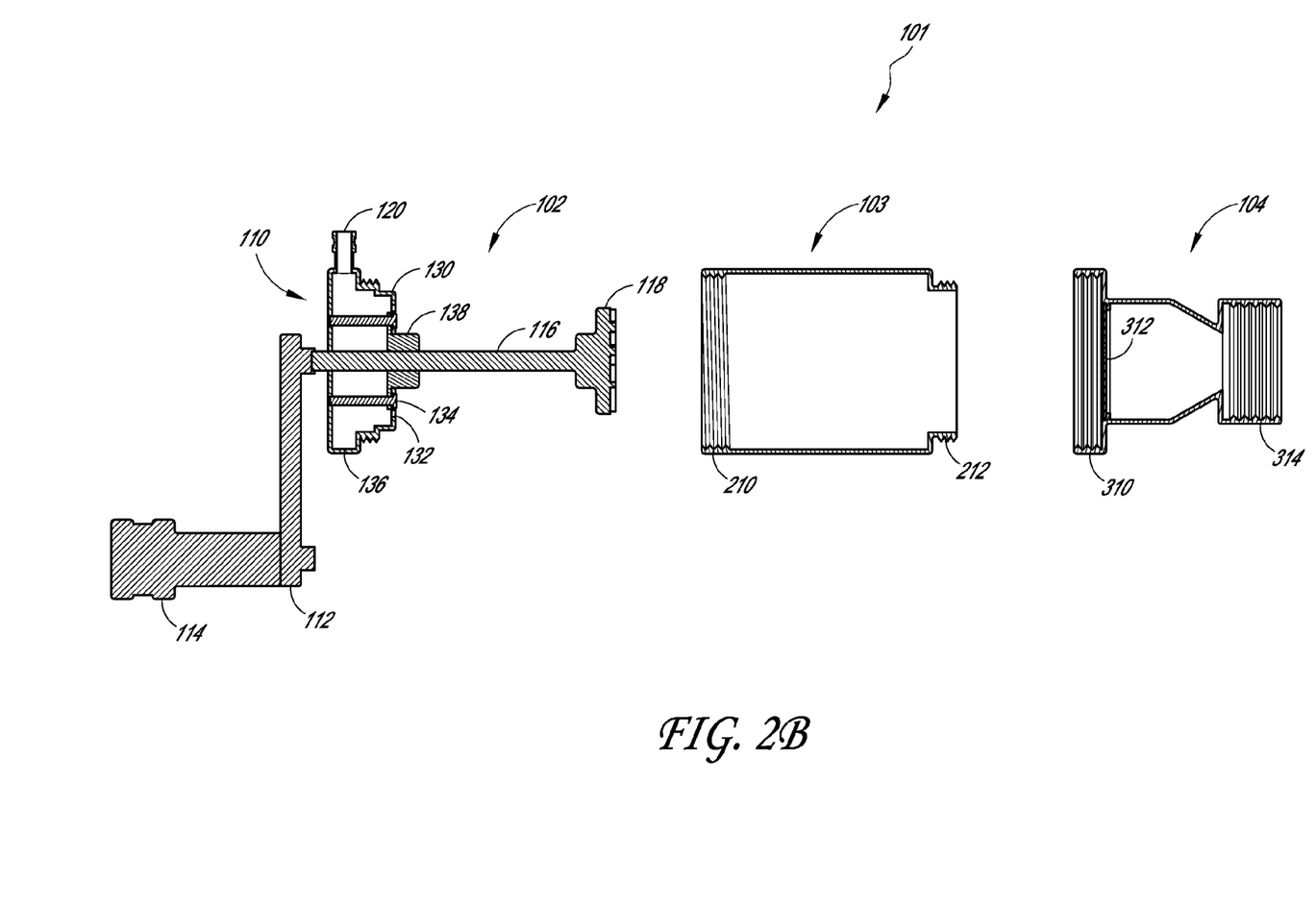

FIG. 1A illustrates a perspective view of an embodiment of a tissue grinding device 101, while FIG. 1B illustrates an exploded view of the same device 101. Cross-sectioned views of an embodiment of the device 101 are also illustrated in FIGS. 2A-B. The device 101 may be used to isolate lymphocytes from tissue, in particular splenic tissue. The tissue grinding device 101 may be constructed from multiple pieces configured to attach or mate to each other, and in one embodiment comprises a top portion 102, a middle portion 103, and a bottom portion 104. In some embodiments, however, the device 101 may be constructed as a single unit.

Preferably, the device 101 is constructed from a sterilizable material such as metal or plastic. In some embodiments, the device 101 is constructed so as to be reusable, which may be beneficial, for example, if the device 101 is to be used in developing countries where access to disposable devices is difficult. In such embodiments, it may be preferable for the device 101 to be constructed from a metal such as steel or aluminum that may be autoclaved or otherwise sterilized for reuse. In other embodiments, the device 101 may be constructed so that all or part of the device may be disposed after use. Such embodiments may thus only require that the device 101 be durable enough for a single use, and it may in some embodiments be constructed at least in part from a plastic.

The top portion 102 comprises a lid 110, which is preferably configured to attach, join, or mate with a proximal end 210 of the middle portion 103, and may comprise threads or latches configured to secure both parts together. When the top portion 102, middle portion 130, and bottom portion 104 are attached together, they define an interior cavity 106, which is preferably dimensioned to accept a tissue sample. As discussed herein, the tissue sample may be all or part of a spleen removed from a patient.

A crank 112 is preferably rotatably attached to the lid 110. In a preferred embodiment, the crank 112 is provided with a handle 114 configured to permit an operator to turn the crank 112, but in some embodiments all or part of the handle 114 may be replaced with a motor or such device capable of rotating the crank 112. The crank 112 is rotatably attached to a proximal end of a crankshaft 116, which extends in a longitudinal direction through the lid 110. A grinder implement 118 is preferably attached at the distal end of the crankshaft 116, and will be discussed further below in relation to FIG. 3. Because the grinder implement 118 rotates, the cavity 106 is preferably cylindrical.

Similarly as with the top portion 102 and middle portion 103, the distal end 212 of the middle portion 103 and a proximal end 310 of the bottom portion 103 are preferably configured to attach, join, or mate together, for example, using threads or latches. A filtering component 312 such as a sieve is preferably provided in the bottom portion 104, and provides a surface for the grinder implement 118 to push against tissue placed within the cavity 106. A distal end 314 of the bottom portion 104 is preferably configured to attach to or be received into a receptacle 320 to receive a tissue slurry.

Figure 3A:
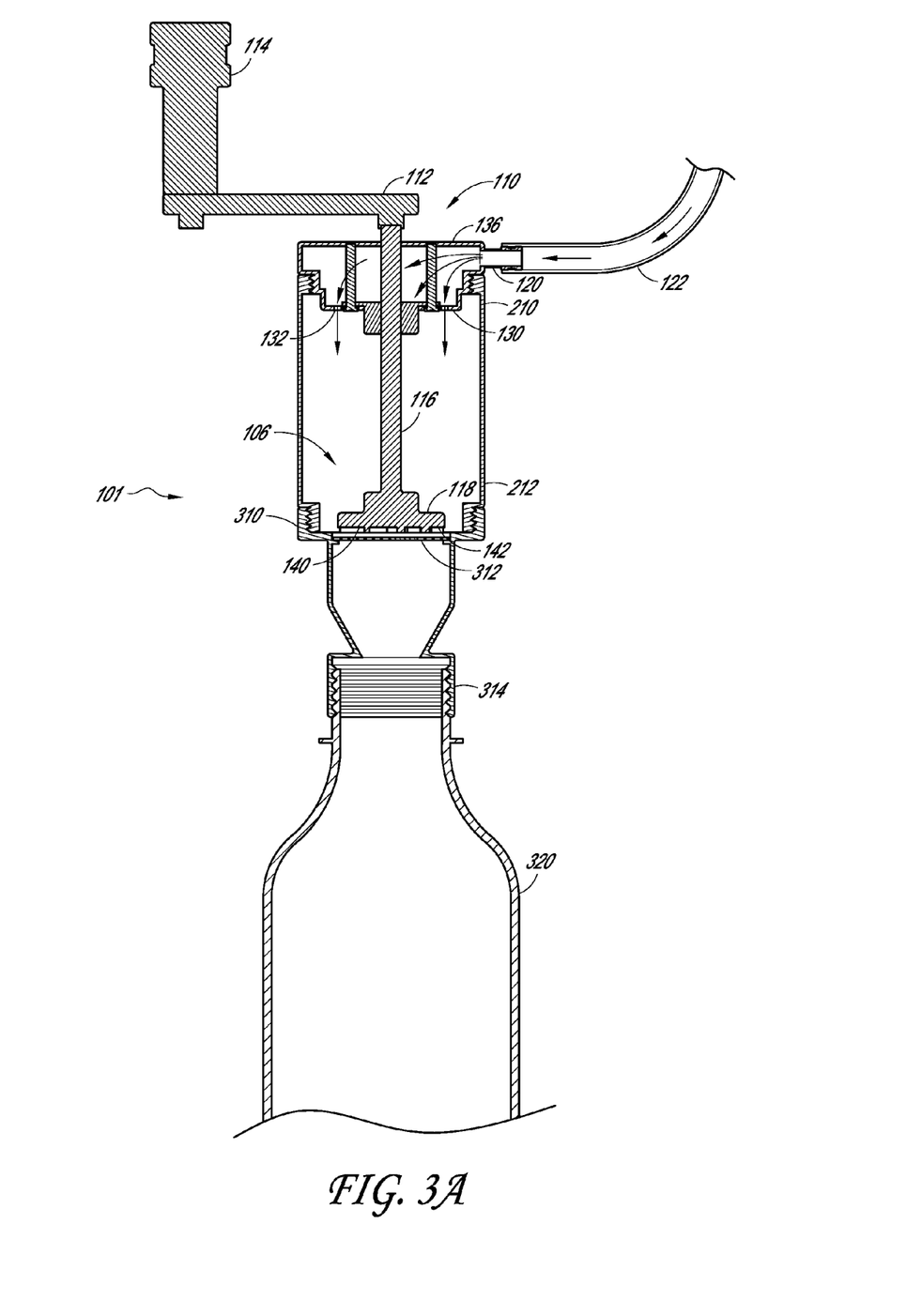
FIGS. 3A-B illustrate views of an embodiment of a tissue grinding device connected to a fluid source.
Figure 3B:
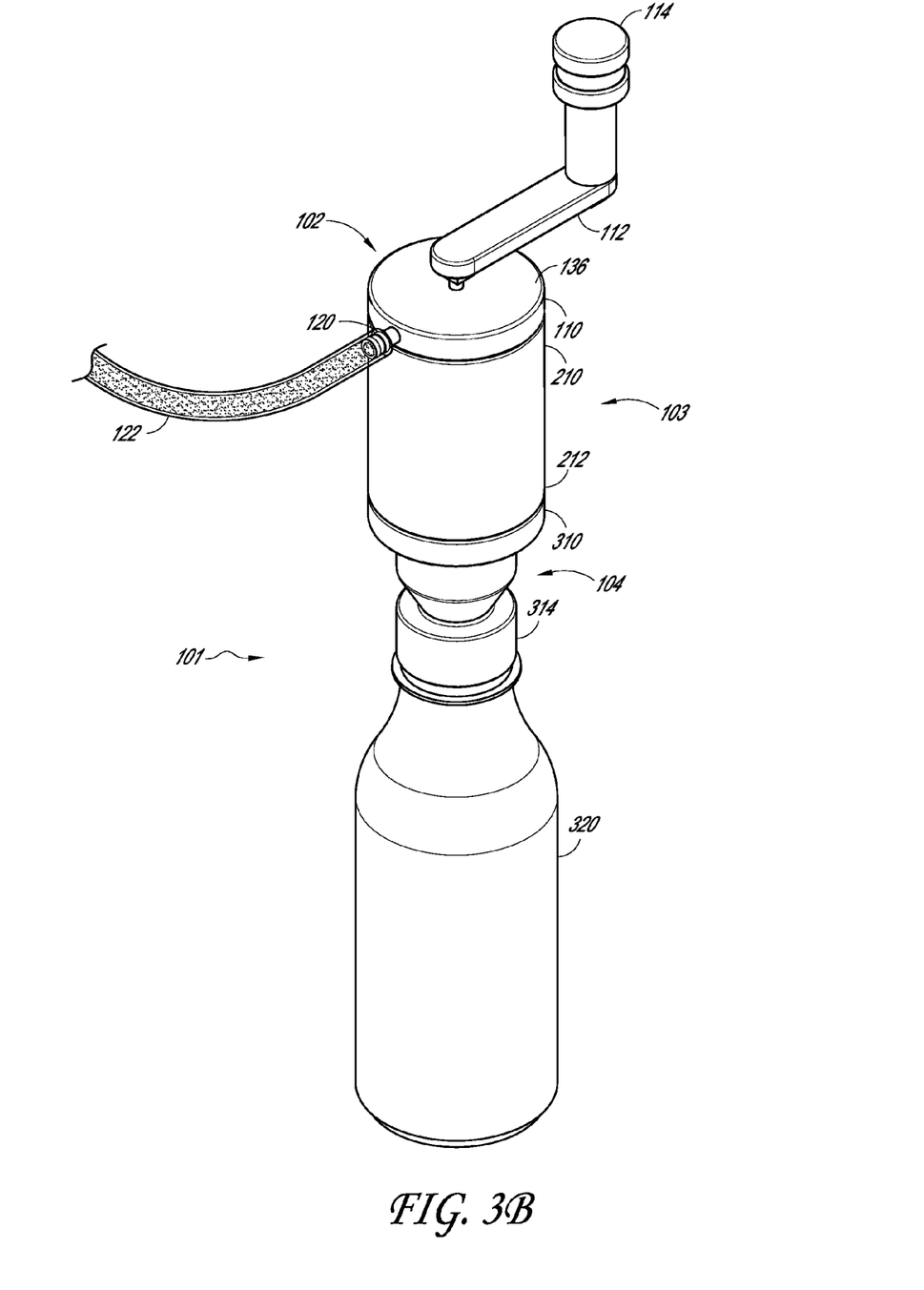

As illustrated in FIGS. 3A-B, a port 120 may be provided on the lid 110, for example a top lid portion 136, so as to permit a fluid such as a wash solution or buffer (e.g., saline, phosphate buffer saline ("PBS")) to be supplied therethrough, for example via a supply conduit 122. In a preferred embodiment, the fluid is PBS with 5% fetal calf serum at pH 7.2, as described below in relation to example 1. This fluid may help flush or move tissue out of the cavity 106. This aspect will be described in further detail below in relation to FIG. 4. Preferably, the receptacle 320, which may be, for example, a sterile bottle, is secured to the distal end 314 of the bottom portion 104. Of course, the port 120 may not necessarily be provided on the lid 110, but may be for example be provided onto the middle portion 103 or bottom portion 104.

Figure 4:
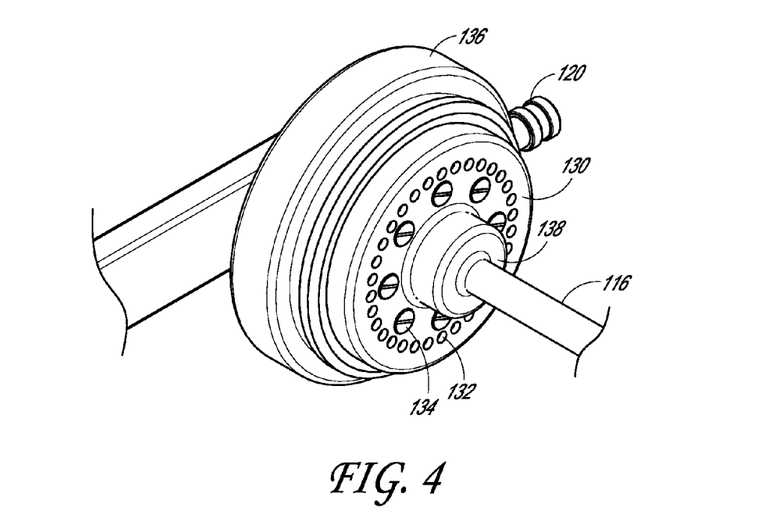
FIG. 4 illustrates the underside of a lid of an embodiment of a tissue grinding device.

FIG. 4 illustrates a closeup view of an embodiment of an underside 130 of the lid 110. Here, the underside 130 is provided with multiple channels 132 to allow the fluid supplied via the port 120 to enter into the cavity 106. Screws 134 are shown here serving as fixation mechanisms to attach the underside 103 to the lid 136. Of course, the underside 130 may be attached using other means, such as welding or riveting.

Figure 5:
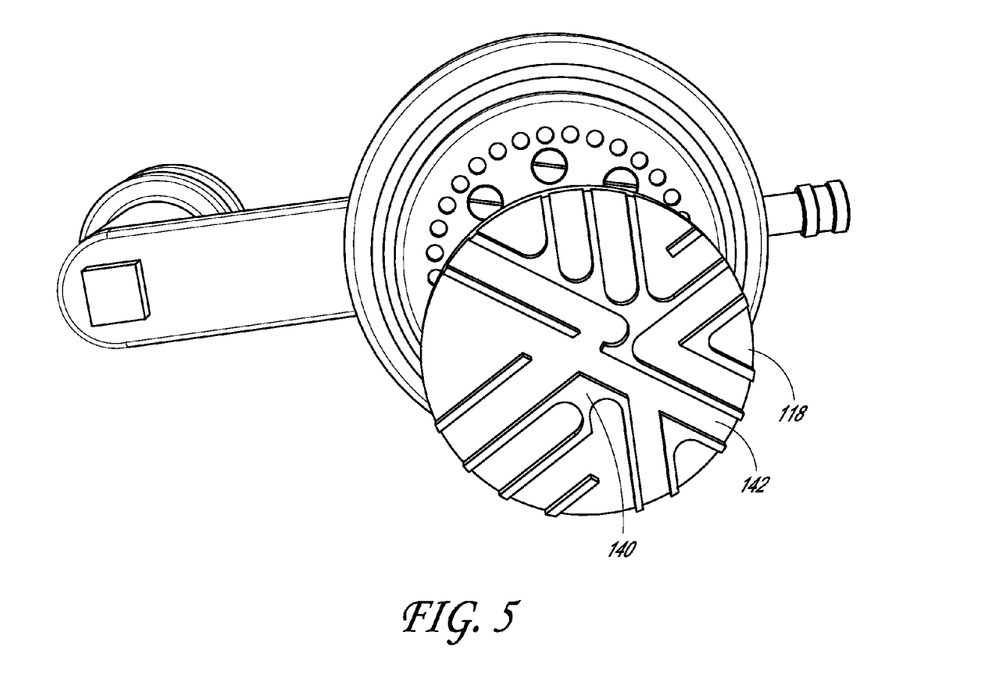
FIG. 5 illustrates the underside of an embodiment of a grinder implement.

With reference now to FIG. 5, an embodiment of a grinder implement 118 is illustrated as viewed from a distal end. The grinding surface 140 of the grinder implement 118 is preferably configured to press and grind tissue placed within the cavity 106 against the filtering component 312 in the bottom portion 104. Preferably, the grinder implement 118 is of a slightly smaller diameter than the cavity 106 so as to permit fluid entering the cavity 106 (for example via the channels 132) to reach the tissue sample. In some embodiments, the grinder implement 118 may be provided with one or more through channels that can permit fluid to reach the tissue being ground by the grinding surface 140.

The grinding surface 140 preferably comprises one or more cutting channels 142 which may be formed, for example via machining, to form sharp edges that can cut, grind, or macerate tissue. Blades or other cutting implements may also be attached to the grinding surface 140. In some embodiments, and as illustrated here, the one or more cutting channels 142 abut with the outer perimeter of the grinder 118, and as such allow the fluid supplied via the channels 132 to reach a greater portion of the tissue sample being ground. Preferably, the grinder implement 118, or at least grinding surface 140, is provided with cutting channels 142 or other cutting implements that are constructed from a suitably hard and durable material such as a metal, ceramic, or hardened plastic that may cut, grind, or macerate tissue without being substantially dulled, weakened, or broken while doing so. Additionally, these should be suitably hard and durable in conjunction with any grinding media, such as grinding beads or grit, that may be used.

Figure 6:
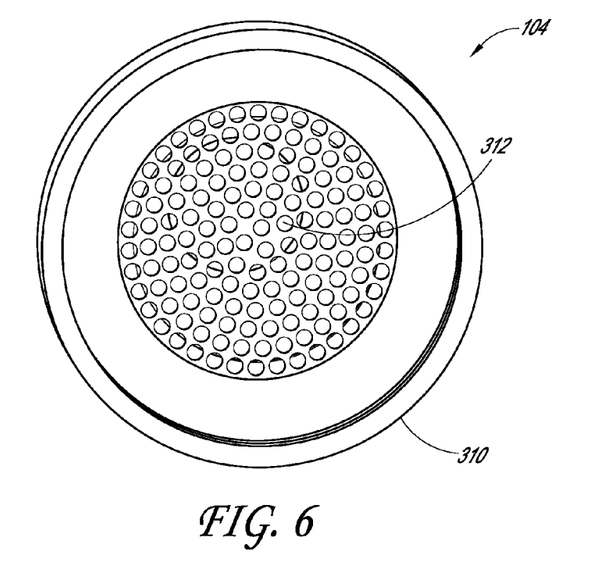
FIG. 6 is an illustration along the proximal end of an embodiment of a bottom portion of a tissue grinding device.

FIG. 6 illustrates a view along the proximal end 310 of the bottom portion 104. The proximal end 310 is configured to mate with the distal end 212 of the middle portion 103 (not illustrated here), and may comprise threads or other securement mechanisms disposed thereon. The filtering component 312 may be attached, for example along its outer perimeter, to an inner wall of the bottom portion 104. In some embodiments, however, the filtering component 312 may be attached to the middle portion 103. The filtering component 312 may provide multiple functions. First, it preferably acts as a solid surface for the grinder implement 118 to press against the tissue sample inserted into the cavity 106. Second, it is preferably provided with one or more apertures that are small enough to prevent fibrous components from the tissue sample from passing through it, while being large enough to permit cells such as lymphocytes to pass through. In some embodiments, the filtering component may have apertures measuring between 500 µm to 5 mm, preferably 2 to 4 mm, and even more preferably 3 mm.

In some embodiments, the filtering component 312 is removable, and in other embodiments the filtering component 312 is fixed or permanently attached to the body of the bottom portion 104, for example via welding. In some embodiments, in particular those provided with a removable filtering component 312, the filtering component 312 may comprise multiple sub-components. For example, a first filtering component 312a may be mechanically stronger and be provided with larger apertures under which a second filtering component 312b may be situated. The second filtering component 312b could for example be less mechanically strong and able to withstand pressure from the grinder implement g, thus requiring that it be positioned under a stronger first filtering component 312a, but may be provided with smaller apertures to promote more efficient filtering. The second filtering component 312b, could, in some embodiments, be a membrane filter. In some embodiments, the filtering component 312 may comprise other attachments or devices for separating cells such as lymphocytes from a homogenized tissue medium, including flow cytometry (including fluorescence-activated cell sorting ("FACS")), and affinity purification (e.g., via antibodies).

Figure 7:
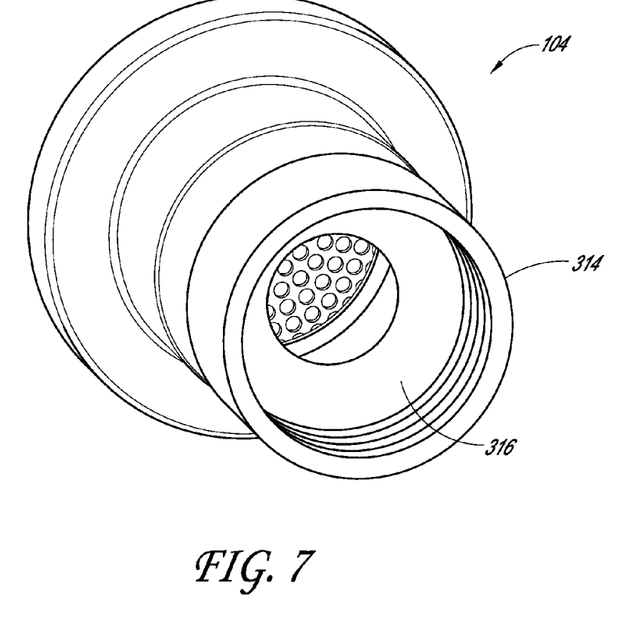
FIG. 7 is an illustration of the distal end of an embodiment of a bottom portion of a tissue grinding device.

FIG. 7 illustrates a view along the distal end 314 of the bottom portion 104. This view illustrates the attachment mechanism for attaching the bottom portion 104 to the collection device 320. Preferably, the attachment mechanism comprises threads configured to secure to the collection device 320. In some embodiments, the collection device 320 is a sterile bottle, for example the bottle illustrated in FIGS. 3A-B. A sealing mechanism, such as an o-ring 316 may also be provided to prevent leakage of fluids in the junction between the attachment mechanism and the collection device 320.

In use, the device 101 may be assembled substantially as illustrated in FIGS. 1A-B. A tissue sample, such as all or part of a spleen, may then inserted into the cavity 106, which is accessible when the top portion 102 is removed from the middle portion 103. Optionally, grinding media may be added to the cavity 106. The top portion 102 is then replaced over the middle portion 103 and secured thereto. The crankshaft 116 is then moved in a longitudinal direction downward until the grinder implement 118 makes contact with the tissue sample, thereby pressing it against the filtering component 312. The crank 112 and/or crankshaft 116 may then be rotated, for example via the handle 114 (or using a motor attached to either the crank 112 or the crankshaft 116), thereby cutting and grinding the tissue within the cavity 106. Optionally, fluid such as a wash solution or buffer may be supplied via a conduit 122 attached to the port 120. This fluid exits the top portion 102 via the channels 132 so as to enter into the cavity 106 and to the tissue being ground. Macerated tissue then passes through the filtering component 312 for collection into a receptacle such as the receptacle 320. As previously mentioned, other assays may also be performed onto the cell extract, including flow cytometry and purification of other extracted cellular constituents.

EXAMPLES

The examples described below illustrate non-limiting experiments conducted to demonstrate the efficacy of lymphocyte reinfusion after splenectomy.

Example 1

Animal Study Splenectomy

Balb/C infant female mice (Sasco, Omaha, Nebr.) weighing 20-25 grams were acquired for the purposes of the example. The mice were free from pathogens and kept in filter isolation throughout the course of study. They were housed in an accredited animal care facility at the University of Missouri-Columbia, and placed on a routine photoperiod with a regular temperature and given laboratory chow and water, all under standard guidelines.

The mice (excluding the control group) were then selected for splenectomy. The operative procedures were performed after the animal was induced with 2% halothane anesthesia and oxygen, and maintained on a constant flow of oxygen with 0.80% halothane delivered via a nose cone.

The abdomens of the mice were cleansed with Betadine solution and shaved. A midline abdominal incision was made, bringing the spleen into the field of view. The spleen was then removed, after cauterizing attached vessels, and placed in a sterile solution of PBS (NaCl 8 g/L, KCl 0.2 g/L, $NaHPO_4$ 1.15 g/L, $KHPO_4$ 0.2 g/L, pH 7.2) with 5% fetal calf serum ("FCS") (SIGMA, St. Louis, Mo.) and kept on ice. The control group had the spleen mobilized and placed back into position without any other disruption. Incisional wounds were closed in two layers and further secured with surgical skin staples.

Example 2

Isolation of Splenic Lymphocytes

The spleens removed from the mice in Example 1 were then cut into 2 mm×2 mm squares and placed on a cell sorter sieve made from steel wire mesh and together placed over a 60×15 petri dish. Using a circular grinding motion, the pieces were pressed against the screen with the plunger of a 10 ml. syringe using PBS with 5% FCS for irrigation until mostly fibrous tissue remained on the screen. Of course, it will be recognized that the tissue grinding device illustrated above in relation to FIGS. 1-7 may preferably be used.

The solution was then centrifuged for ten minutes in a Beckman rotor at 1500 rpm, and the supernatant discarded. The pellet was resuspended in 10 ml of ACK lysing buffer ($NH_4Cl$ 8.29 g/L, $KHCO_4$ 1 g/L, $Na_4EDTA$ 37.2 mg/L, pH 7.2) and incubated for five minutes at room temperature with occasional shaking. Another 10 ml of PBS/5% FCS buffer was added and the solution was centrifuged again for ten minutes at 1500 rpm, followed by discarding of the supernatant. The resulting pellet was washed in PBS/5% FCS twice, each time centrifuging for ten minutes at 1500 rpm. Finally, the pellet was resuspended in a 5 ml PBS/5% FCS buffer, placed onto 20 ml of Ficoll/Paque gradient (Pharmacia LKB, Piscataway, N.J.) and centrifuged for 20 minutes at 1500 rpm with brakes off. The interphase layer was then aspirated out and washed in PBS (pH7.22) three times. A cell sample stained with Trypan blue was placed on a haemocytometer and examined under the microscope for purity, viability, and counts.

Example 3

Preparation and Inoculation with Nonviable *Streptococcus Pneumoniae* Cells

*Streptococcus pneumoniae* Type III cells were purchased from ATCC (Bethesda, Md.). These cells were inoculated into tryptic soy broth (Difco Labs Detroit, Mich.), previously adjusted to pH 7.7, and grown for 4-6 hours at 37° C. Formaldehyde was added to a concentration of 0.1% and the cell suspension was stored at 4° C. after being washed three times in PBS (pH 7.2). Prior to use, the cultured cells were washed 3× in sterile PBS and centrifuged into a pellet. They were also test plated onto chocolate agar to ensure nonviability and tested for presence of a capsule with an India ink stain and Quellung positive with *Pneumococcus* type III specific antisera (Difco, Detroit, Mich).

The mice from Example 1 were then immunized with $1\times10^3$ of the prepared nonviable *Streptococcus pneumoniae* cells intravenously, using McFarland nepholometry for quantification.

Example 4

Antibody Measurements

Polysaccharide antigens were coupled to protein for adsorption in accordance with the procedure set forth by Gray (Gray, B., ELISA methodology for polysaccharide antigens: Protein coupling of polysaccharides for adsorption to plastic tubes, Journal of Immunological Methods, 28: 187-19.2, 1979).

Briefly, three test tubes A-C were prepared such that tube A had 0.5 ml of 0.05N NaOH with 0.001% phenolpthalein, tube B had 1 mg of cyanuric chloride crystals, and tube C had 0.1 ml of 0.2% poly-1-lysine (MW 54,000, Sigma Chemicals, St. Louis, Mo.). A polysaccharide (Pnuimmune, Lederle Labs, Pearl River, N.Y.) solution of 100 μl (2.5 mg/ml) was alkalinized for 10 sec. by swirling in tube A. Activation was then accomplished by pouring the contents of tube A into tube B and swirled the contents for ten seconds, at which point the solution turned colorless. The test tube contents were then coupled to poly-1-lysine in tube C and refrigerated at 4° C. for 2 hrs. Coupled polysaccharide was diluted in a 1:4 ratio in PBS (pH 7.2) and eventually used for adsorption onto enzyme-linked immunosorbent assay ("ELISA") plates to test for antibody titers as described below.

Blood was then obtained from each mouse in Example 1 via retro-orbital venous plexus, prior to immunization, and every seven days after immunization for six weeks. Sera was separated from the blood samples and stored at −20° C.

Antibody titers against *Strep. pneumoniae* polysaccharide were quantified by ELISA. ELISA plates were coated with 50 μl. of pneumococcal polysaccharide vaccine coupled to poly-1-lysine. Plates were then incubated at 37° C. for two hours and then washed three times in PBS with 0.5% Tween. All free sites on the plate were blocked using PBS-Tween (0.5%)-Gelatin(1%) and incubated at 37° C. for two hours. The plates were rinsed again 3' in PBS-Tween(0.5%). Subsequently, 50 μl of mouse antiserum (diluted 1/1000) was added to each well and incubated overnight at 4° C. All wells were again washed three times in PBS-Tween(0.05%). Next, 50 μl of a 1/100 dilution of goat anti-mouse Ig antisera linked to alkaline phosphatase was added to each well and incubated at 37° C. for one hour. All wells were rinsed three times in PBS-Tween(0.05%). Finally, 50 μl of p-nitrophenol phosphate (1 mg/ml) (Sigma Chemicals, St. Louis, Mo.) in diethanolamine buffer (pH 9.6) was added to each well and incubated for 30 min. prior to reading on an ELISA reader. (Dynatech).

Example 5

Analysis and Results

Figure 8:
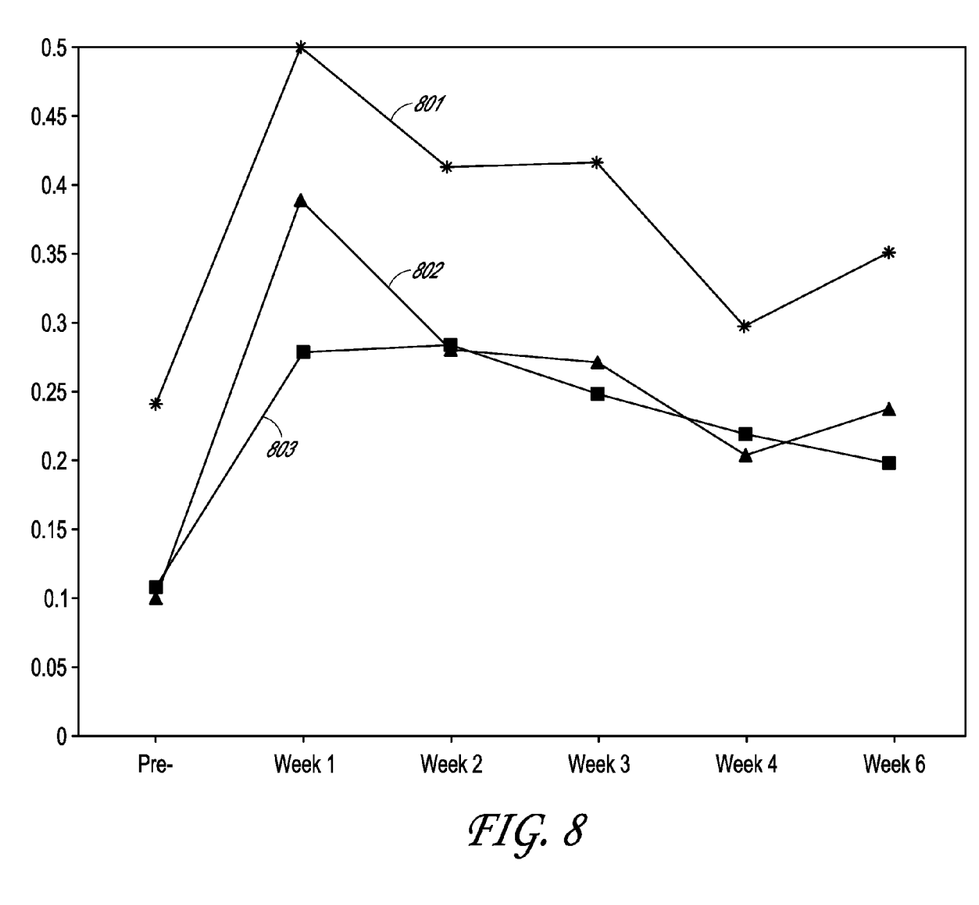
FIG. 8 is a graph of antibody titers after subcutaneous vaccination with *Streptococcus pneumoniae* polysaccharide antigen.

FIG. 8 illustrates the resulting antibody titers as a result of subcutaneous polyvalent vaccination with 1 μg. of *Streptococcus pneumoniae* polysaccharide antigen from Example 3. The antibody titers here and in FIGS. 9 and 10 were tested against *Streptococcus* polysaccharide conjugated to ELISA plates.

This figure plots absorbance on the y-axis versus time on the x-axis. The absorbance directly relates to antibody titer in mouse serum. The antibody titers of the control (unsplenectomized) group are illustrated as line 801. Similarly, line 802 illustrates the splenectomized group where splenic lymphocytes were reinfused. Line 803 meanwhile illustrates the antibody titers of the splenectomized group with no reinfusion of splenic lymphocytes.

In all groups, peak antibody titers were reached in the period around one week after immunization. Nonsplenectomized animals, illustrated in line 801, demonstrated higher antibody titers in reaction to the *Strep. pneumoniae* vaccination compared to the splenectomized mice in lines 802 and 803. The splenectomized group with splenic lymphocyte reinfusion, in line 802, had an elevated immune response at one week compared with the group without splenic lymphocytes.

Without wishing to be bound by theory, it is believed that the reinfused splenic lymphocytes provided to the splenectomized group strengthened the humoral immune response, as the spleen may serve as a repository for certain subsets of lymphocytes, for example B cells, that may be reactive to antigens such as polysaccharide antigens. Here, the splenectomized group receiving a reinfusion of splenic lymphocytes exhibited a greater immune response, in particular of the humoral immune response, compared to splenectomized mice not receiving a reinfusion of splenic lymphocytes.

Of course, other antigens may be administered to increase the immunity after splenectomy. Vaccines, in particular polysaccharide vaccines, may be administered. Some vaccines that may be administered to increase immunity after splenectomy include without limitation vaccines against *Haemophilus influenzae*, *Streptococcus pneumoniae*, and *Neisseria meningitides*. Although the antigen in this example was administered subcutaneously, other administration routes are also possible, including via intramuscular, intravenous, oral, and other such administration routes.

Figure 9:
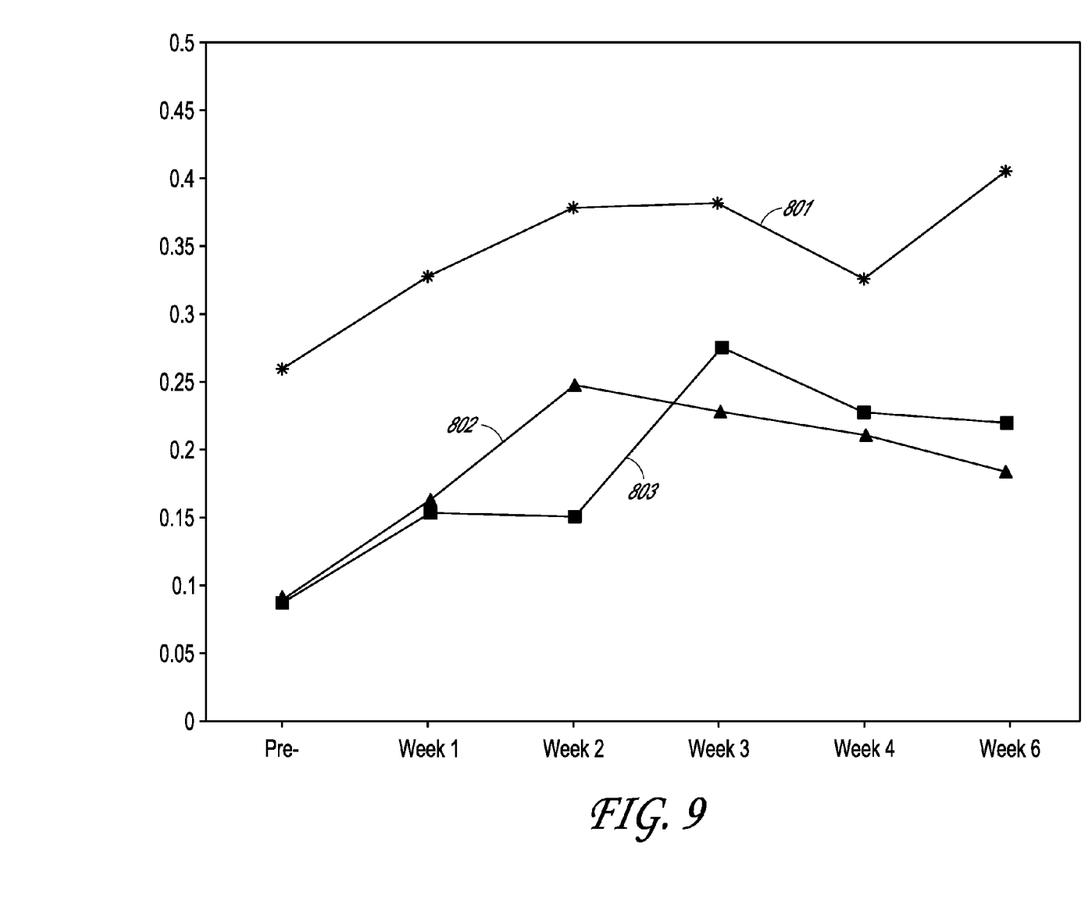
FIG. 9 is a graph of basal antibody titers without exposure to antigen.

FIG. 9 illustrates the basal antibody titer of three groups of mice where no antigen was administered. As before, the unsplenectomized control group is illustrated as line 801, while the splenectomized group with reinfused lymphocytes is illustrated as line 802. The splenectomized group with no reinfusion is illustrated as line 803.

In this figure, while the unsplenectomized group shows a higher basal antibody titer against *Streptococcus pneumoniae*, the splenectomized group which underwent splenic lymphocyte reinfusion (line 802) showed an elevated antibody titer compared to the group in line 803 for the first two weeks, after which the antibody titers become similar.

This figure also indicates that intact spleens result in a higher basal antibody secretion against *Streptococcus pneumoniae*, most likely due to the spleen harboring a subpopulation of cells responsible for recognizing this antigen. Accordingly, improved methods of readministering cells extracted from splenic tissue may improve humoral immunity after splenectomy.

Figure 10:
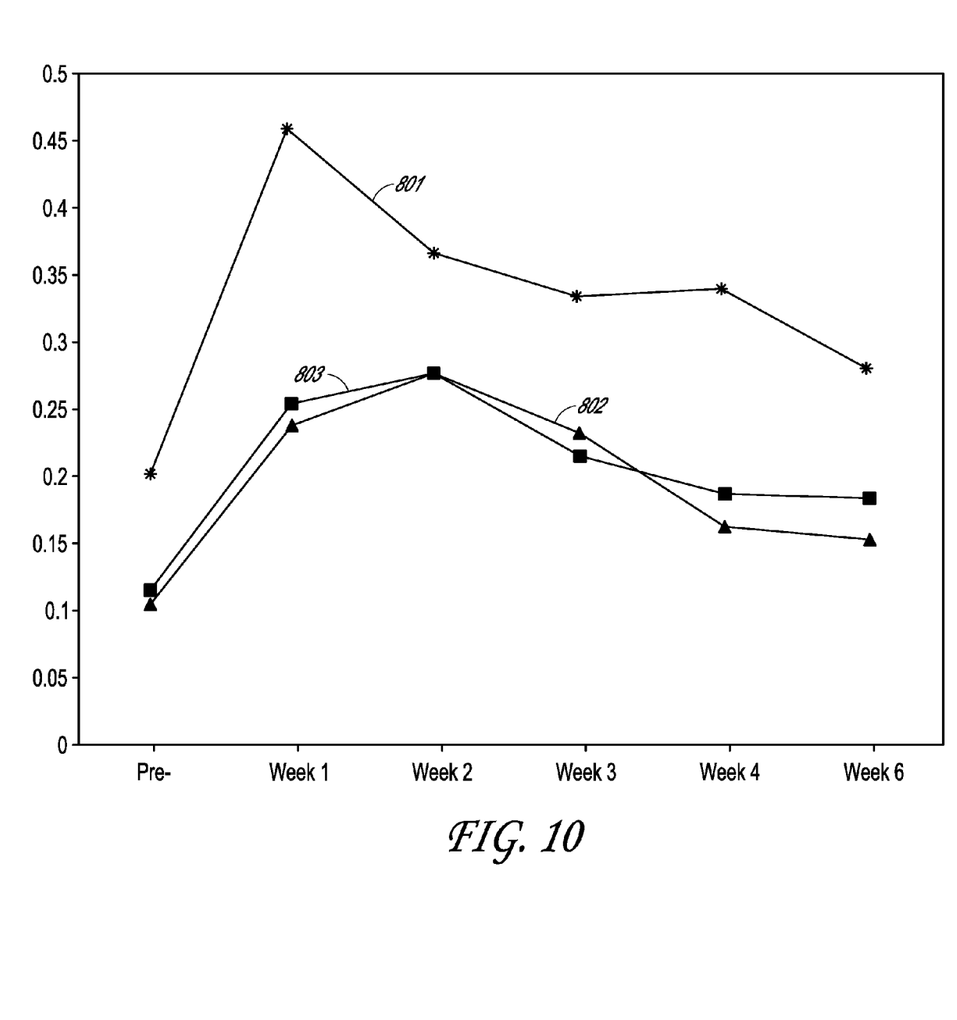
FIG. 10 is a graph of antibody titers after intravenous administration of killed *Streptococcus pneumoniae* cells.

FIG. 10 illustrates the antibody titer of three groups of mice which were intravenously administered with killed *Streptococcus pneumoniae* Type III cells. The lines denote the same groups used in the previous figures. Here, the unsplenectomized control group exhibits an elevated antibody response at one week. Both of the splenectomized groups (with and without reinfused splenic lymphocytes) show a lower, yet somewhat elevated, response peaking approximately two weeks after administration of killed cells.

Without wishing to be bound by theory, these results indicate the possibility of a more involved mechanism of response towards T-dependent antigens (e.g., bacteria, virus-infected cells, tumor cells) not easily rectified by a reinfusion of lymphocytes. Increased immunity may involve both the structure of the spleen in conjunction with the reticuloendothelial system, or a lack of pre-existing antibodies that may be used to opsonize the killed cells. However, studies have shown that the spleen is responsible for only a small portion of the clearance for T-dependent antigens such as bacteria compared to the liver and other organs. As such, post-splenectomy cellular immunity may be improved by immunization prior to the splenectomy, as antibodies against T-dependent antigens would then permit such antigens to be cleared without the spleen.

Accordingly, the cell-mediated immunity after splenectomy may be increased by reinfusion of lymphocytes that had been previously exposed or challenged to a T-dependent antigen. For example, the immune response in Figure C for the splenectomized mice receiving a lymphocyte reinfusion may be increased if the mice had received a prior vaccination or exposure to killed *Streptococcus pneumoniae* cells prior to splenectomy.

Further, immunity—in particular cell-mediated immunity—against tumor or cancerous cells may also be increased by reinfusion of splenic lymphocytes. It is believed that there is a population of splenic cells that may be responsible for additional protection against tumor cells. For example, one study has identified that certain splenic cells may react to a Streptococcal preparation inactivated with penicillin G may identify and destroy liver tumor cells when a spleen is present. The reinfusion of splenic lymphocytes may thus boost immune response to tumor or cancerous cells after splenectomy.

Although this invention has been disclosed in the context of certain embodiments and examples, those skilled in the art will understand that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes or embodiments of the disclosed invention. Thus, it is intended that the scope of the present invention herein disclosed should not be limited by the particular disclosed embodiments described above.

What is claimed is:

1. A method of reducing likelihood of post-splenectomy infection in a patient, the method comprising:
   removing all or part of the patient's spleen; and
   harvesting intact lymphocytes from at least a portion of the removed spleen;
   administering the intact harvested lymphocytes to the patient, thereby increasing the patient's immunity and reducing the likelihood of post-splenectomy infection.

2. The method of claim 1, wherein the lymphocytes are administered intravenously.

3. The method of claim 1, wherein the step of harvesting comprises homogenizing at least a portion of the removed spleen and isolating a cellular fraction containing lymphocytes from the homogenized splenic tissue.

4. The method of claim 1, further comprising testing at least a sample of the harvested splenic lymphocytes after harvesting for one or more of purity, cellular viability, and cellular counts.

5. The method of claim 1, further comprising administering an antigen associated with a pathogen subsequent to removal of the spleen from the patient, wherein the patient has a need to reduce a likelihood of infection by the pathogen.

6. The method of claim 5, wherein the antigen is a vaccine.

7. The method of claim 6, wherein the method improves the vaccine response of the patient.

8. The method of claim 7, wherein the improved vaccine response comprises improving the humoral immunity of the patient.

9. The method of claim 5, wherein the antigen is administered subcutaneously.

10. The method of claim 5, wherein the antigen comprises a polysaccharide antigen.

11. The method of claim 5, wherein the antigen comprises a *Streptococcus pneumoniae* vaccine.

12. The method of claim 5, wherein the antibody titer of the patient to the antigen one week after administration of the antigen is elevated.

* * * * *